US00PP08206P

United States Patent [19]

Holtkamp, Sr.

[11] Patent Number: Plant 8,206

[45] Date of Patent: Apr. 20, 1993

[54] AFRICAN VIOLET PLANT NAMED TAMA

[76] Inventor: Reinhold Holtkamp, Sr.,
Blumenstrasse 28, D 4242
Rees-Haffen, Fed. Rep. of Germany

[21] Appl. No.: 736,503

[22] Filed: Jul. 26, 1991

[51] Int. Cl.[5] ..... A01H 5/00
[52] U.S. Cl. ..... Plt./69.1
[58] Field of Search ..... Plt./69.1, 69.2

*Primary Examiner*—James R. Feyrer

*Attorney, Agent, or Firm*—Foley & Lardner

[57] ABSTRACT

A new and distinct cultivar of African violet named Tama characterized by its single violet-shaped, pearl color flowers with light pink center; strong, upright flower stems that curve slightly toward the center to form a compact bouquet above the leaves; medium green, oval leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Tama.

The new cultivar was referred to during the breeding and selection process by the designation 824/87 and is a product of a planned breeding program. The new cultivar was originated from a cross made by me in the controlled breeding program in Haffen, Federal Republic of Germany. The female, or seed parent was a cultivar designated J 84/7. The male, or pollen parent was a cultivar designated H/53/III.

Tama was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Tama has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Tama, which in combination distinguish this African violet as a new and distinct cultivar:

(1) Strong, upright flower stems curving slightly toward the center.

(2) Single violet-shaped, pearl color flowers with light pink center.

(3) Profuse flowering.

(4) Each plant carries 6–9 and more upright flower stems each of which carries 8–10 and more flowers.

(5) Long lasting, non-dropping flowers.

(6) Vigorous and compact grower.

(7) Plant saleable 10 to 11 weeks after potting.

(8) Seed capsules push slightly through.

(9) Medium green, oval leaves.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn.

Botanical classification: *Saintpaulia ionantha,* Ramat., c.v. Tama.

Parentage:

*Male parent.*—H 53/III.

*Female parent.*—J 87/7.

Propagation: The new cultivar holds its distinguishing characteristics through successive propagations by leaf cuttings.

Plant: From 8 cm to 11 cm tall when grown in pots, and 22–26 cm in diameter when fully grown.

Leaves:

*General form.*—Oval.

*Diameter.*—55–60 mm wide and 65–75 mm long.

*Texture.*—Leatherlike.

*Aspect.*—Hairy, slightly shiny.

*Veins.*—Upperside: visible; underside: well pronounced, light green, shiny.

*Color (upperside).*—Yellow-Green Group 147 A.

*Color (underside).*—Greyed-Purple Group 186 C.

*Petiole.*—Strong upright, green with purplish brown touch, hairy.

Flowers:

*Buds.*—Bell-shaped, greenish white, 5–7 mm just before opening.

*Sepals.*—Five (5). Color: Brownish green.

*Calyx.*—Shape: Funnel-shaped. Aspect: Spear-shaped, hairy.

*Peduncle.*—Character: Strong upright, hairy. Color: Green with purplish brown touch.

Individual flowers:

*Size.*—38–43 mm.

Shape.—Single violet-shaped, slightly frilled edges.

*Color* (*upperside*).—White Group 155 C with center being Purple Group 75 B to C. The small petal edges occasionally are Yellow-Green Group 145 D and lighter. Under cooler temperatures and more intensive lighting, the light pink in the center tends to intensify.

*Color* (*underside*).—White Group 155 C.

*Borne.*—Each flower stem carries 8–10 and more flowers on strong, upright peduncles that are free standing above the leaves, thereby forming a compact bouquet.

*Flowering habit.*—Flowers 10–11 weeks after potting.

Reproductive organs:

*Stamens.*—Two (2).

*Anthers.*—2 composed of 4 l anther cells, seed capsules push slightly through.

*Filaments.*—Yellowish green, 3–4 mm long.

*Pollen color.*—Yellow Group 7 A.

*Styles.*—6–7 mm long, pearl color, base of ovary light green and hairy.

Roots: Normally developed, white when young, turning slightly brownish when older.

Disease resistance: Up to date, Tama has shown very good resistance to all major violet diseases.

GENERAL OBSERVATIONS

Tama is an attractive, vigorous grower with medium green, oval leaves. A tight bouquet of flowers free standing above the leaves develops after 10–11 weeks. Each of the 6–9 and more strong flower stems carries 8–10 and more pearl color flowers with a light pink center. The single violet-shaped flowers have slightly frilled edges and are long-lasting and non-dropping. The seed capsules push slightly through.

I claim:

1. A new and distinct cultivar of African violet named Tama, as described and illustrated, and particularly characterized by its single violet-shaped, pearl color flowers with light pink center; strong, upright flower stems that curve slightly toward the center to form a compact bouquet above the leaves; medium green, oval leaves; profuse flowering, vigorous and compact growth habit, flowering 10–11 weeks after potting, and its long lasting and non-dropping flowers.

* * * * *

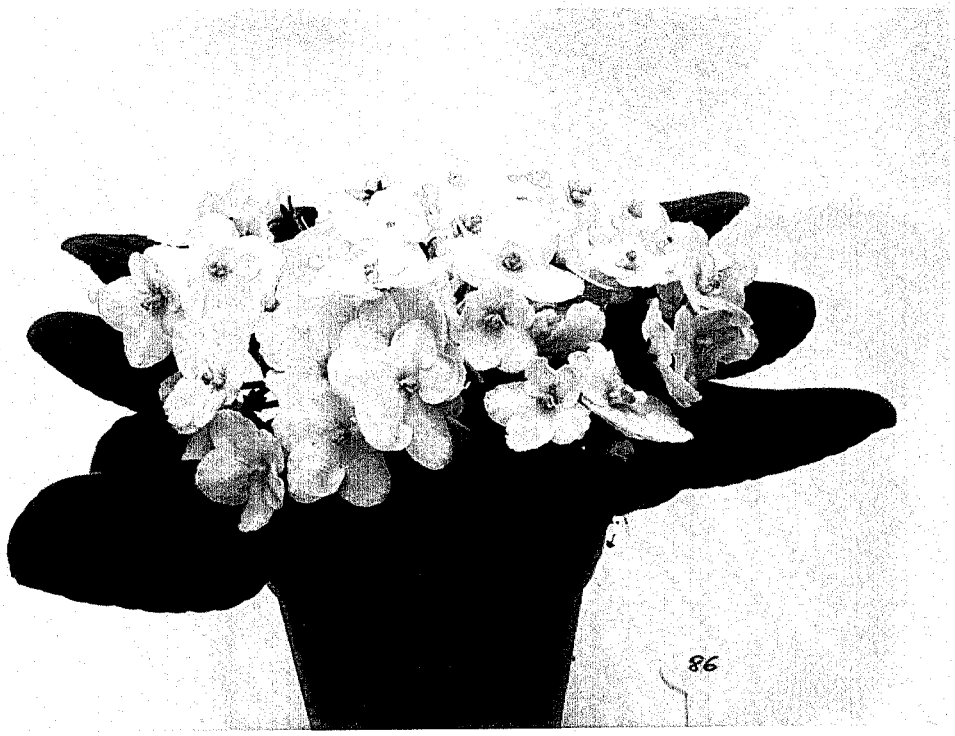
86